US008304576B2

(12) United States Patent
Ishii et al.

(10) Patent No.: US 8,304,576 B2
(45) Date of Patent: Nov. 6, 2012

(54) PROCESS FOR PRODUCTION OF HALOGENATED ALPHA-FLUOROETHERS

(75) Inventors: Akihiro Ishii, Kawagoe (JP); Manabu Yasumoto, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 86 days.

(21) Appl. No.: 12/994,669

(22) PCT Filed: May 14, 2009

(86) PCT No.: PCT/JP2009/058967
§ 371 (c)(1),
(2), (4) Date: Nov. 24, 2010

(87) PCT Pub. No.: WO2009/145063
PCT Pub. Date: Dec. 3, 2009

(65) Prior Publication Data
US 2011/0082313 A1    Apr. 7, 2011

(30) Foreign Application Priority Data
May 29, 2008  (JP) ................................ 2008-141119

(51) Int. Cl.
C07C 59/00 (2006.01)
C07C 43/00 (2006.01)
C07C 31/34 (2006.01)
(52) U.S. Cl. .................. 562/586; 568/842; 568/615
(58) Field of Classification Search .......... None
See application file for complete search history.

(56) References Cited

U.S. PATENT DOCUMENTS 3,981,927 A *   9/1976   Siegemund et al. .......... 568/683
4,972,040 A    11/1990   Robin et al.
2008/0125589 A1*  5/2008   Ishii et al. ..................... 544/318

FOREIGN PATENT DOCUMENTS

| JP | 50-76007 | 6/1975 |
|---|---|---|
| JP | 2-104545 A | 4/1990 |
| JP | 2006-290870 A | 10/2006 |

OTHER PUBLICATIONS

Informal Comments including English language translation transmitted on Jul. 21, 2009 (Seven (7) pages).
Theodora W. Greene, et al., "Protective Groups in Organic Synthesis", Third Edition, 1999, John Wiley & Sons, Inc.
Akihiro Ishii, et al. "Yukigoseikyokaishi", 1999, pp. 102-103, vol. 57, No. 10, Japan.
Internationl Search Report including partial including English language translation dated Jul. 21, 2009 and PCT/ISA/237 Form (Six (6) pages).
Fluorine Pharmacy—Foundation and Experiment—, edited by Y. Kobayashi, I. Kumadaki, T. Taguchi, Hirokawa Publishing Co., 1993, p. 214.
Funabiki et al., Enamine-assisted facile generation of trifluoroacetaldehyde from trifluoroacetaldehyde ethyl hemiacetal and its carbon-carbon bond forming reaction leading to β-hydroxy-β-trifluoromethyl ketones, Chem. Commun. (England), 1998, pp. 2051-2052.
Skiles et al., Inhibition of Human Leukocyte Elastase (HLE) by N-Substituted Peptidyl Trifluromethyl Ketones, J. Med. Chem. (America), 1992, vol. 35, pp. 641-662.

* cited by examiner

Primary Examiner — Karl J Puttlitz
(74) Attorney, Agent, or Firm — Crowell & Moring LLP

(57) ABSTRACT

Halogenated α-fluoroethers (or bis-derivatives thereof) can be produced by reacting a halogenated hemiacetal (or bis-derivative thereof) with sulfuryl fluoride ($SO_2F_2$) in the presence of an organic base. The reaction is conducted preferably in the presence of "a salt or complex of an organic base with hydrogen fluoride", whereby the objective dehydroxyfluorination can proceed extremely favorably. It is still preferable to use as the starting substrate a halogenated hemiacetal prepared from fluoral or 3,3,3-trifluoropyruvic acid ester. Thus, industrially important halogenated α-fluoroethers can be industrially produced with high selectivity and in high yield.

7 Claims, No Drawings

PROCESS FOR PRODUCTION OF HALOGENATED ALPHA-FLUOROETHERS

TECHNICAL FIELD

The present invention relates to a process for industrially producing halogenated α-fluoroethers which are important as an intermediate of medicines or agrichemicals or as a flon alternative compound.

BACKGROUND OF THE INVENTION

Halogenated α-fluoroethers, the object of the present invention, serve as an important intermediate of medicines or agrichemicals or as an important flon alternative compound. Particularly, α,β,β,β-tetrafluoroethers are utilized as a useful intermediate for a volatile anaesthetic "desflurane". As conventional techniques for such α-fluoroethers, relating to the present invention, the following two techniques are exemplified.

There have been disclosed: a process for reacting fluoral hemiacetals with the Yarovenko's reagent (Patent Publication 1); and a process consisting of two process steps in which fluoral hemiacetals are converted into corresponding p-toluenesulfonic acid esters and then these are reacted with fluoride anion ($F^-$) (Patent Publication 2).

REFERENCES ABOUT PRIOR ART

Patent Publication
Patent Publication 1: Japanese Patent Application Publication No. 50-76007
Patent Publication 2: Japanese Patent Application Publication No. 2-104545

SUMMARY OF THE INVENTION

An object of the present invention is to provide a process for industrial production of halogenated α-fluoroethers.

Patent Publication 1 in which the Yarovenko's reagent is used as a dehydroxyfluorination agent requires previously preparing the reagent from chlorotrifluoroethylene and diethylamine. Furthermore, a fluorine-containing organic waste is stoichiometrically formed as a by-product, so that an industrial execution thereof had been difficult.

In Patent Publication 2 where the reaction is achieved with two process steps, the operations including a post-treatment are so complicated that a high productivity cannot be expected. Additionally, the total yield is also not satisfying.

Thus, there has been intensely desired a production process which can be readily and industrially accomplished and provide halogenated α-fluoroethers with high productivity and yield.

As a result of eager studies the present inventors have made in view of the above, they have newly found it possible to produce halogenated α-fluoroethers represented by the general formula [2] by reacting halogenated hemiacetals represented by the general formula [1] with sulfuryl fluoride in the presence of an organic base. Furthermore, there has been also newly found that the present reaction can be applied to bis-derivatives formed through alkylene group (in which halogenated α-fluoroether bis-derivatives represented by the general formula [2a] are obtained as the objective by using halogenated hemiacetal bis-derivatives represented by the general formula [1a] as the starting substrate).

Incidentally, the present applicant has found a dehydroxyfluorination reaction of alcohols by combination of sulfuryl fluoride ($SO_2F_2$) and the organic base and has already filed an application therefor [International Publication 2006/098444 Pamphlet (Japanese Patent Application Publication No. 2006-290870)]. On the other hand, the raw materials of the present invention are relatively unstable "halogenated hemiacetals" or bis-derivatives thereof. These can be said to be "an equivalent of a compound having a carbon with which two hydroxyl groups are concurrently bonded". The present inventors have made it clear: that these raw material compounds are reacted with sulfuryl fluoride ($SO_2F_2$) in the presence of the organic base thereby selectively subjecting "free hydroxyl group" alone to fluorine substitution; and that, as opposed to this, $-OR^2$ group, $[-O-(CH_2)_n-O-]$ group and haloalkyl group are inducted into the halogenated α-fluoroethers represented by the general formula [2] or the halogenated α-fluoroether bis-derivatives represented by the general formula [2a] with high yield without being subjected to any change.

Moreover, the present invention allows the reaction to be conducted with one process step as a one-pot reaction, in which fluorosulfuric acid-esterification of the starting substrate halogenated hemiacetals (or the bis-derivatives thereof) and a succeeding fluorine substitution proceed continuously. In fluorine substitution, "a salt or complex of an organic base with hydrogen fluoride" formed as a by-product in the reaction system by the fluorosulfuric acid-esterification is usefully utilized as a fluoride anion source. (see Scheme 1 showing an example where the halogenated hemiacetals represented by the general formula [1] are used as the starting substrate.)

SCHEME 1

[Chemical Formula 1]

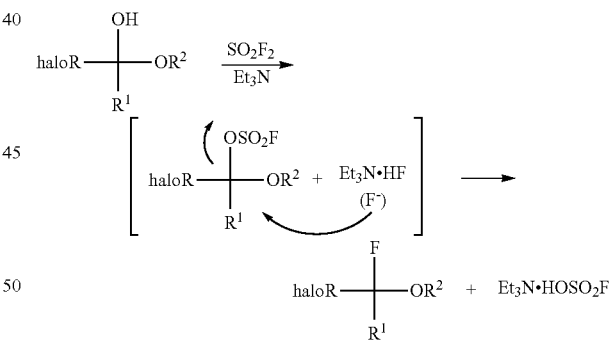

An example of a case where triethylamine (1 equivalent) is used as an organic base.

In the present invention, it has also been made clear that the succeeding fluorine substitution enormously excellently proceeds by conducting the reaction in the additional presence of "a salt or complex of an organic base with hydrogen fluoride" in the system (see Scheme 2 showing an example where the halogenated hemiacetals represented by the general formula [1] are used as the starting substrate.) The fluorosulfuric acid-esterification of the relatively unstable halogenated hemiacetals proceeds excellently even in the presence of "a salt or complex of an organic base with hydrogen fluoride", which is a new finding.

SCHEME 2

[Chemical Formula 2]

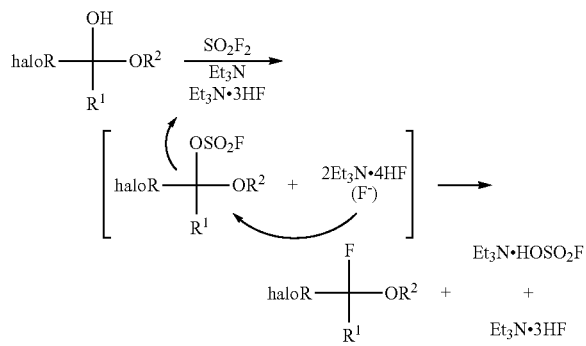

An example of a case where triethylamine (1 equivalent) is used as an organic base while triethylamine tris(hydrogen fluoride) complex (1 equivalent) is used as "a salt or complex of an organic base with hydrogen fluoride".

Furthermore, the present invention have newly made it clear that hemiacetals of fluoral (corresponding to halogenated hemiacetals represented by the general formula [3]) or hemiacetals of 3,3,3-trifluoropyruvic acid esters (corresponding to halogenated hemiacetals represented by the general formula [5]) are extremely preferable starting substrates. When using such starting substrates, the desired reaction can excellently proceed under mild conditions and the objective halogenated α-fluoroethers are obtained with high selectivity and yield. These starting substrates can be readily prepared from fluoral or 3,3,3-trifluoropyruvic acid esters (either of which is readily available in large-scale) so as to be suitable also from the viewpoint of a starting substrate for an industrial production process. Particularly, α,β,β,β-tetrafluoroethyl-metnylether obtained from fluoral methyl hemiacetal are useful as an intermediate for a volatile anaesthetic "desflurane", so as to be particularly preferable.

Thus, an extremely useful process has been found as a process for industrially producing the halogenated α-fluoroethers, thereby achieving the present invention.

More specifically, the present invention includes the following $1^{st}$ process to $7^{th}$ process and provides an industrial production process of the halogenated α-fluoroethers.

According to the present invention, there is provided a process for producing halogenated α-fluoroethers represented by the general formula [2]

[Chemical Formula 4]

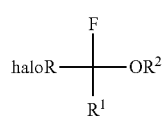

[2]

by reacting halogenated hemiacetals represented by the general formula [1]

[Chemical Formula 3]

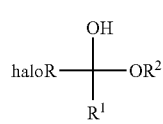

[1]

with sulfuryl fluoride ($SO_2F_2$) in the presence of an organic base (a $1^{st}$ process).

[In the formulas: haloR represents haloalkyl group; $R^1$ represents hydrogen atom, alkyl group, substituted alkyl group, alkoxycarbonyl group or substituted alkoxycarbonyl group; and $R^2$ represents alkyl group or substituted alkyl group.]

According to the present invention, there is further provided a process for producing halogenated α-fluoroether bis-derivatives represented by the general formula [2a]

[Chemical Formula 6]

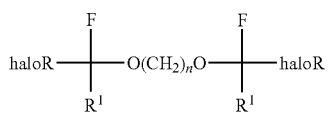

[2a]

by reacting halogenated hemiacetal bis-derivatives represented by the general formula [1a]

[Chemical Formula 5]

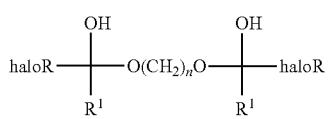

[1a]

with sulfuryl fluoride ($SO_2F_2$) in the presence of an organic base (a $2^{nd}$ process).

[In the formulas: haloR mutually independently represents a haloalkyl group; $R^1$ mutually independently represents a hydrogen atom, an alkyl group, a substituted alkyl group, an alkoxycarbonyl group or a substituted alkoxycarbonyl group; and n represents an integer of from 2 to 18.]

The $1^{st}$ or $2^{nd}$ process may be a process for producing halogenated α-fluoroethers or halogenated α-fluoroether bis-derivatives, the process being characterized in that the reaction is conducted in the additional presence of "a salt or complex of an organic base with hydrogen fluoride" in a system (a $3^{rd}$ process).

According to the present invention, there is further provided a process for producing halogenated α-fluoroethers represented by the general formula [4]

[Chemical Formula 8]

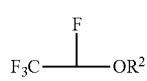

[4]

by reacting halogenated hemiacetals represented by the general formula [3]

[Chemical Formula 7]

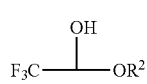

[3]

with sulfuryl fluoride ($SO_2F_2$) in the presence of an organic base (a $4^{th}$ process).

[In the formulas, $R^2$ represents an alkyl group or a substituted alkyl group.]

The 4$^{th}$ process may be a process for producing halogenated α-fluoroethers, the process being characterized in that the reaction is conducted in the additional presence of "a salt or complex of an organic base with hydrogen fluoride" in a system (a 5$^{th}$ process).

According to the present invention, there is further provided a process for producing halogenated α-fluoroethers represented by the general formula [6]

[Chemical Formula 10]

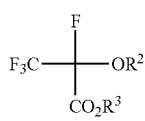

[6]

by reacting halogenated hemiacetals represented by the general formula [5]

[Chemical Formula 9]

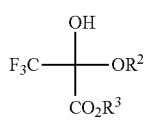

[5]

with sulfuryl fluoride ($SO_2F_2$) in the presence of an organic base (a 6$^{th}$ process).

[In the formulas, $R^2$ and $R^3$ mutually independently represent an alkyl group or a substituted alkyl group.]

The 6$^{th}$ process may be a process for producing halogenated α-fluoroethers, the process being characterized in that the reaction is conducted in the additional presence of "a salt or complex of an organic base with hydrogen fluoride" in a system (a 7$^{th}$ process).

DETAILED DESCRIPTION

Advantageous points of the present invention over conventional techniques will be discussed below.

As compared to Patent Publication 1, a dehydroxyfluorination agent used in the present invention is suitable for large-scale production. Sulfuryl fluoride is widely utilized as a fumigant and industrially available at low cost. Additionally, wastes made in the use of sulfuryl fluoride can be conveniently treated into inorganic salts such as fluorite ($CaF_2$), calcium sulfate, etc., which reduce the load to the environment.

As compared to Patent Publication 2, the reaction can be conducted with one process step (in which fluorosulfuric acid-esterification and a succeeding fluorine substitution proceed continuously as a one-pot reaction) with extremely high productivity and in high yield.

Furthermore, impurities serving as by-products difficult to be separated off are hardly provided in the present invention, so that the objective product can be obtained at a high chemical purity.

Thus, the present invention is a production process which can solve all problems the conventional techniques had carried and can be industrially readily conducted.

A process for producing halogenated α-fluoroethers of the present invention will be discussed in detail.

In the present invention, it is possible to produce halogenated α-fluoroethers represented by the general formula [2] (or halogenated α-fluoroether bis-derivatives represented by the general formula [2a]) by reacting halogenated hemiacetals represented by the general formula [1] (or halogenated hemiacetal bis-derivatives represented by the general formula Rap with sulfuryl fluoride ($SO_2F_2$) in the presence of an organic base.

HaloR as shown in the general formula [1] denotes haloalkyl group. Examples of the haloalkyl group are those obtained by substitution caused on any carbon atom in a linear, branched or cyclic (with a carbon number of not smaller than 3) alkyl group having a carbon number of from 1 to 18 with any number of and any combination of halogen atoms including fluorine, chlorine, bromine and iodine (where the alkyl group causes substitution with at least one halogen atom). Among these, the preferable is fluoroalkyl group and chloroalkyl group, and the more particularly preferable is trifluoromethyl group.

$R^1$ of the halogenated hemiacetals represented by the general formula [1] denotes hydrogen atom, alkyl group, substituted alkyl group, alkoxycarbonyl group or substituted alkoxycarbonyl group. Examples of alkyl moieties of the alkyl group and of the alkoxycarbonyl group (the moieties corresponding to, for example, $R^3$ of the halogenated hemiacetals represented by the general formula [5]) include a linear, branched or cyclic (with a carbon number of not smaller than 3) alkyl group having a carbon number of from 1 to 18.

The alkyl group and the alkoxycarbonyl group may have, on any carbon atom in the alkyl moiety, any number of and any combination of substituents (and correspond to substituted alkyl group and substituted alkoxycarbonyl group, respectively). Examples of the substituents are: halogen atom such as fluorine, chlorine, bromine, iodine, etc.; azide group; nitro group; lower alkyl group such as methyl group, ethyl group, propyl group, etc.; lower haloalkyl group such as fluoromethyl group, chloromethyl group, bromomethyl group, etc.; lower alkoxy group such as methoxy group, ethoxy group, propoxy group, etc.; lower haloalkoxy group such as fluoromethoxy group, chloromethoxy group, bromomethoxy group, etc.; lower alkyl amino group such as dimethylamino group, diethylamino group, dipropylamino group, etc.; lower alkylthio group such as methylthio group, ethylthio group, propylthio group, etc.; cyano group; lower alkoxycarbonyl group such as methoxycarbonyl group, ethoxycarbonyl group, propoxycarbonyl group, etc.; aminocarbonyl group ($CONH_2$); lower alkylaminocarbonyl group such as dimethylaminocarbonyl group, diethylaminocarbonyl group, dipropylaminocarbonyl group, etc.; unsaturated group such as alkenyl group, alkynyl group, etc.; aromatic cyclic group such as phenyl group, naphthyl group, pyrrolyl group, furyl group, thienyl group, etc.; aromatic cyclic oxy group such as phenoxy group, naphthoxy group, pyrrolyloxy group, furyloxy group, thienyloxy group, etc.; aliphatic heterocyclic group such as piperidyl group, piperidino group, morpholinyl group, etc.; protected hydroxyl group; protected amino group (including amino acid and peptide residue); protected thiol group; protected aldehyde group; protected carboxyl group; etc.

Incidentally, in the present specification, each of the following terms is used as having the following meaning. "Lower" means a linear, branched or cyclic (with a carbon number of not smaller than 3) chain having a carbon number of from 1 to 6. In the case that "unsaturated group" is the double bond (alkenyl group), it may be in the form of E configuration, Z configuration or a mixture of these. As "protecting groups of hydroxyl group, amino group (including amino acid and peptide residue), thiol group, aldehyde group and carboxyl group", it is possible to use protecting groups and the like described in Protective Groups in Organic Synthesis, Third Edition, 1999, John Wiley & Sons, Inc. (, in which not less than two functional groups may be protected with one protecting group). Moreover, "unsaturated group", "aromatic cyclic group", "aromatic cyclic oxy group" and "aliphatic heterocyclic group" may be subjected to substitution with halogen atom, azide group, nitro group, lower alkyl group, lower haloalkyl group, lower alkoxy group, lower haloalkoxy group, lower alkyl amino group, lower alkylthio group, cyano group, lower alkoxycarbonyl group, aminocarbonyl group, lower alkylaminocarbonyl group, protected hydroxyl group, protected amino group (including amino acid and peptide residue), protected thiol group, protected aldehyde group, protected carboxyl group or the like.

Among these, hydrogen atom, alkoxycarbonyl group and substituted alkoxycarbonyl group are preferable. Particularly, hydrogen atom and alkoxycarbonyl group are more preferable.

$R^2$ of the halogenated hemiacetals represented by the general formula [1] denotes alkyl group or substituted alkyl group.

The alkyl group and the substituted alkyl group are the same as the alkyl group and the substituted alkyl group as had been discussed as $R^1$ of the halogenated hemiacetals represented by the general formula [1], and can be selected independently of $R^1$.

HaloR and $R^1$ of the halogenated hemiacetal bis-derivatives represented by the general formula [1a] are the same as haloR and $R^1$ as had been discussed on the halogenated hemiacetals represented by the general formula [1]. n represents an integer of from 2 to 18. Among these, with regard to n, an integer of from 2 to 12 is preferable and that of from 2 to 6 in particular is more preferable. Two haloR included in the halogenated hemiacetal bis-derivatives represented by the general formula [1a] are mutually independently selected from the above substituents. However, it is preferable to select the same substituent for the two haloR if taking the preparation of the starting substrate into account. Additionally, the same thing can be said for two $R^1$ of the halogenated hemiacetal bis-derivatives represented by the general formula [1a].

Stereochemistry of the halogenated hemiacetals represented by the general formula [1] will be discussed. In the halogenated hemiacetals, a carbon atom with which hydroxyl group forms a covalent bond is an asymmetric carbon atom with the exception of the case where haloR and $R^1$ adopt the same substituent. In the case where the starting substrate has the asymmetric carbon atom, it is not only allowed to use a racemic form (it will be understood that the racemic form can be used) but also allowed to use an optically active form (R configuration or S configuration), and its optical purity is not limited. A dehydroxyfluorination reaction of the present invention proceeds together with stereochemical reversal, stereochemical maintenance or racemization. This stereoselectivity differs according to the combination of the starting substrate and the organic base and to the adopted reaction conditions, so that the starting substrate, the organic base and the reaction conditions may be suitably selected according to the desired stereochemistry (R configuration, S configuration or racemic form) of the objective halogenated α-fluoroethers represented by the general formula [2]. The same as the stereochemistry of the halogenated hemiacetals represented by the general formula [1] goes for that of corresponding two carbon atoms of the halogenated hemiacetal bis-derivatives represented by the general formula [1a], mutually independently.

The halogenated hemiacetals represented by the general formula [1] (or the halogenated hemiacetal bis-derivatives represented by the general formula [1a]) can be prepared by the conventionally known method. Halogenated hemiacetals represented either by the general formula [3] or by the general formula [5], the particularly preferable starting substrate for the present invention, can be readily prepared from fluoral [$CF_3CHO$ (or an equivalent thereof)] and 3,3,3-trifluoropyruvic acid esters [$CF_3COCO_2R$ (R denotes alkyl group or substituted alkyl group)], respectively. Furthermore, ethylhemiacetal or hydrate of fluoral, and ethyl 3,3,3-trifluoropyruvate are commercially available.

The amount of the used sulfuryl fluoride ($SO_2F_2$) is required only to be not lower than 0.7 mole, preferably from 0.8 to 10 moles in general, more preferably from 0.9 to 5 moles in particular, relative to 1 mole of the halogenated hemiacetals represented by the general formula [1]. In the case of using the halogenated hemiacetal bis-derivatives represented by the general formula [1a] as the starting substrate, it is required only to use it in the same manner in an amount two times that of the halogenated hemiacetals represented by the general formula [1].

As a dehydroxyfluorination agent for the present invention, trifluoromethanesulfonyl fluoride ($CF_3SO_2F$) or perfluorobutanesulfonyl fluoride ($C_4F_9SO_2F$) may be used. However, a conscious employment of these reactants is not so advantageous in view of: their availability in large scale; their fluorine atom economy; waste treatment (by which a fluorine-containing organic waste is stoichiometrically formed as a by-product); etc.

Examples of the organic base for the present invention are trimethylamine, dimethylethylamine, diethylmethylamine, triethylamine, di-n-propylmethylamine, dimethylcyclohexylamine, diisopropylethylamine, tri-n-propylamine, diisopropylisobutylamine, dimethyl-n-nonylamine, tri-n-butylamine, di-n-hexylmethylamine, dimethyl-n-dodecylamine, tri-n-pentylamine, 1,4-diazabicyclo[2.2.2] octane (DABCO), dimethylaminopyridine (DMAP), 1,5-diazabicyclo[4.3.0] non-5-ene (DBN), 1,8-diazabicyclo[5.4.0]undec-7-ene (DBU), pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, 3,5,6-collidine, etc.

Among these, the preferable are triethylamine, dimethylcyclohexylamine, diisopropylethylamine, tri-n-propylamine, tri-n-butylamine, pyridine, 2,3-lutidine, 2,4-lutidine, 2,6-lutidine, 3,4-lutidine, 3,5-lutidine, 2,4,6-collidine and 3,5,6-collidine. The more preferable are triethylamine, diisopropylethylamine, tri-n-propylamine, tri-n-butylamine, pyridine, 2,4-lutidine, 2,6-lutidine, 3,5-lutidine and 2,4,6-collidine, in particular. These organic bases may be used singly or in combination. Additionally, an organic base having a carbon number of not less than 8 is high in fat-solubility so as to be readily recovered at a post-treatment using water, thereby being reused without being lowered in reactivity. Accordingly, such an organic base is suitable for an industrial production process. In the present specification, "carbon number" means the total number of carbon atoms contained in an organic base.

The amount of the used organic base is required only to be not lower than 0.7 mole, preferably from 0.8 to 15 moles in general, more preferably from 0.9 to 10 moles in particular, relative to 1 mole of the halogenated hemiacetals represented by the general formula [1]. In the case of using the halogenated hemiacetal bis-derivatives represented by the general formula [1a] as the starting substrate, it is required only to use it in the same manner in an amount two times that of the halogenated hemiacetals represented by the general formula [1].

Then, "a salt or complex of an organic base with hydrogen fluoride" to be used in the $3^{rd}$ process, the $5^{th}$ process and the $7^{th}$ process will be discussed in detail.

Examples of the organic base of "a salt or complex of an organic base with hydrogen fluoride" include trimethylamine, dimethylethylamine, diethylmethylamine, triethylamine, di-n-propylmethylamine, dimethylcyclohexylamine, diisopropylethylamine, tri-n-propylamine, diisopropylisobutylamine, dimethyl-n-nonylamine, tri-n-butylamine, di-n-hexylmethylamine, dimethyl-n-dodecylamine, tri-n-pentylamine, 1,4-diazabicyclo[2.2.2]octane (DABCO), dimethylaminopyridine (DMAP), 1,5-diazabicyclo[4.3.0] non-5-ene (DBN), 1,8-diazabicyclo[5.4.0]undec-7-ene (DBU), pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, 3,5,6-collidine, etc.

Among these, the preferable are triethylamine, dimethylcyclohexylamine, diisopropylethylamine, tri-n-propylamine, tri-n-butylamine, pyridine, 2,3-lutidine, 2,4-lutidine, 2,6-lutidine, 3,4-lutidine, 3,5-lutidine, 2,4,6-collidine and 3,5,6-collidine. The more preferable are triethylamine, diisopropylethylamine, tri-n-propylamine, tri-n-butylamine, pyridine, 2,4-lutidine, 2,6-lutidine, 3,5-lutidine and 2,4,6-collidine in particular.

The mole ratio of the organic base of "a salt or complex of an organic base with hydrogen fluoride" to hydrogen fluoride is within a range of from 100:1 to 1:100, preferably within a range of from 50:1 to 1:50 in general, and more preferably within a range of from 25:1 to 1:25 in particular. Furthermore, it is convenient to use "a complex comprising 1 mole of triethylamine and 3 moles of hydrogen fluoride" and "a complex comprising up to 30% (up to 10 mol %) of pyridine and up to 70% (up to 90 mol %) of hydrogen fluoride", both of which are placed on sale from Aldrich (Aldrich, 2007-2008 Comprehensive Catalogue).

The amount of "a salt or complex of an organic base with hydrogen fluoride" to be used is required only to be not less than 0.3 mole as fluoride anion ($F^-$), preferably within a range of from 0.5 to 50 moles in general and more preferably within a range of from 0.7 to 25 moles in particular, relative to 1 mole of the halogenated hemiacetals represented by the general formula [1]. When using the halogenated hemiacetal bis-derivatives represented by the general formula [1a] as the starting substrate, it is required only to use it in the same manner in an amount two times that of the halogenated hemiacetals represented by the general formula [1].

Examples of a reaction solvent are: aliphatic hydrocarbons such as n-hexane, cyclohexane, n-heptane, etc.; aromatic hydrocarbons such as benzene, toluene, ethylbenzene, xylene, mesitylene, etc; halogenated hydrocarbons such as methylene chloride, chloroform, 1,2-dichloroethane, etc; ethers such as diethyl ether, tetrahydrofuran, diisopropyl ether, tert-butyl methyl ether, etc; esters such as ethyl acetate, n-butyl acetate, etc; amides such as N,N-dimethylformamide, N,N-dimethylacetamide, N-methylpyrrolidone, 1,3-dimethyl-2-imidazolidinone, etc; nitriles such as acetonitrile, propionitrile, etc; and dimethylsulfoxide, etc.

Among these, the preferable are n-hexane, n-heptane, toluene, xylene, mesitylene, methylene chloride, tetrahydrofuran, diisopropyl ether, tert-butyl methyl ether, ethyl acetate, N,N-dimethylformamide, N,N-dimethylacetamide, acetonitrile, propionitrile and dimethylsulfoxide. Particularly, the more preferable are toluene, xylene, methylene chloride, tetrahydrofuran, diisopropyl ether, ethyl acetate, N,N-dimethylformamide and acetonitrile. It is possible to use these reaction solvents singly or in combination. Furthermore, the present invention may be performed without the solvent.

In the case of using the reaction solvent, the amount thereof is required only to be not less than 0.1 L (liter), preferably within a range of from 0.2 to 10 L in general, and more preferably within a range of from 0.3 to 5 L in particular, relative to 1 mole of the halogenated hemiacetals represented by the general formula [1] (or the halogenated hemiacetal bis-derivatives represented by the general formula [1a]).

The temperature condition is required only to be conducted within a range of from −100 to +100° C., preferably within a range of from −60 to +60° C. in general, more preferably within a range of from −50 to +50° C. in particular. In the case of conducting the reaction under a temperature condition of not lower than the boiling point of sulfuryl fluoride (−49.7° C.), it is possible to use a pressure-proof reaction vessel.

The pressure condition is required only to be conducted within a range of from atmospheric pressure to 2 MPa, preferably within a range of from atmospheric pressure to 1.5 MPa in general, more preferably within a range of from atmospheric pressure to 1 MPa in particular. Therefore, it is preferable to conduct the reaction in the use of a pressure-proof reaction vessel made of a material such as stainless steel (SUS) or glass (glass lining). Furthermore, for infusion of sulfuryl fluoride in large-scale, the effective is a process for causing a negative pressure in a pressure-proof reaction vessel first of all, and then introducing gaseous or liquid sulfuryl fluoride into therein while recovering the pressure under a reduced pressure.

The reaction time is within 72 hours; however, it differs according to the combination of the starting substrate and the organic base and to the adopted reaction conditions. It is therefore preferable to determine a temporal point at which the starting substrate is generally completely consumed as the endpoint of the reaction, upon tracking the progress of the reaction by an analytical means such as gas chromatography, thin layer chromatography, liquid chromatography, nuclear magnetic resonance (NMR), etc. The objective halogenated α-fluoroethers represented by the general formula [2] (or the halogenated α-fluoroether bis-derivatives represented by the general formula [2a]) can be obtained by conducting an usual operation on a reaction-terminated liquid as a post-treatment. The objective product can be purified at a high chemical purity by activated carbon treatment, distillation, recrystallization, column chromatography or the like as necessary.

Such an operation as to directly distill the reaction-terminated liquid is particularly effective. By conducting such a post-treatment (defluorination, fractional distillation or the like, as necessary), it becomes possible to obtain a product of quality sufficient either for an intermediate of medicines or agrichemicals or for a flon alternative compound.

In the present invention, the halogenated hemiacetals represented by the general formula [1] (or the halogenated hemiacetal bis-derivatives represented by the general formula [1a]) are reacted with sulfuryl fluoride in the presence of the organic base, thereby producing the halogenated α-fluoroethers represented by the general formula [2] (or the halogenated α-fluoroether bis-derivatives represented by the general formula [2a]).

It is preferable to conduct the reaction in the presence of "a salt or complex of an organic base with hydrogen fluoride", by which the objective dehydroxyfluorination reaction can proceed extremely favorably.

It is more preferable to use, as the starting substrate, halogenated hemiacetals represented by the general formula [3] or the general formula [5] and able to be prepared from fluoral or 3,3,3-trifluoropyruvic acid esters. With this, the industrially important halogenated α-fluoroethers can be industrially produced with high yield and selectivity.

EXAMPLES

Embodiments of the present invention are specifically explained by examples. The present invention is, however, not limited to these examples. Incidentally, omission marks discussed in the examples are as follows.
Et; Ethyl group
Me; Methyl group

Example 1

A pressure-proof reaction vessel made of stainless steel (SUS) was charged with 500 mg (3.47 mmol, 1.00 eq) of halogenated hemiacetals represented by the following formula

[Chemical Formula 11]

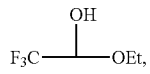

3.5 mL of acetonitrile, 1.756 mg (17.35 mmol, 5.00 eq) of triethylamine and 839 mg (5.20 mmol, 1.50 eq) of triethylamine tris(hydrogen fluoride) complex, followed by immersing it in a coolant bath of −78° C. Then, 708 mg (6.94 mmol, 2.00 eq) of sulfuryl fluoride ($SO_2F_2$) was blown thereinto by using a bomb, followed by stirring at room temperature throughout the night. The reaction-terminated liquid was confirmed by $^1$H-NMR and $^{19}$F-NMR to have a conversion rate and a selectivity of 100% and not less than 70%, respectively. By directly distilling the reaction-terminated liquid (at normal pressure), halogenated α-fluoroethers represented by the following formula

[Chemical Formula 12]

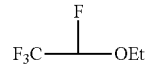

can be obtained as a mixture of triethylamine and acetonitrile. The yield was confirmed by the conversion rate and the selectivity of the reaction-terminated liquid to be not less than 70%. A molecular weight of 147 (M+1) was observed by GC-MS (CI method). $^1$H-NMR and $^{19}$F-NMR will be discussed below.

$^1$H-NMR [Standard substance; $(CH_3)_4Si$, Deuteration solvent; $CDCl_3$]; δ ppm/1.34 (t, 7.0 Hz, 3H), 3.86 (m, 1H), 4.03 (m, 1H), 5.41 (dq, 61.9 Hz, 3.0 Hz, 1H).

$^{19}$F-NMR [Standard substance; $C_6F_6$, Deuteration solvent; $CDCl_3$]; δ ppm/19.60 (dq, 61.9 Hz, 6.4 Hz, 1F), 78.03 (dd, 6.4 Hz, 3.0 Hz, 3F).

Example 2

In conformity with YUKIGOSEIKYOKAISHI (Japan), 1999, Vol. 57, No. 10, p. 102-103, fluoral (gas) was generated from an excessive amount of fluoral monohydrate, followed by blowing it into allyl alcohol. Stirring was conducted for 2 hours at room temperature, thereby obtaining halogenated hemiacetals represented by the following formula

[Chemical Formula 13]

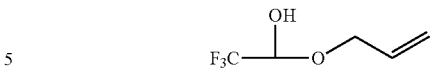

at a quantitative yield.

A pressure-proof reaction vessel made of stainless steel (SUS) was charged with 1.56 g (9.99 mmol, 1.00 eq) of halogenated hemiacetals represented by the above formula, 10 mL of acetonitrile, 4.05 g (40.02 mmol, 4.01 eq) of triethylamine and 1.61 g (9.99 mmol, 1.00 eq) of triethylamine tris(hydrogen fluoride) complex, followed by immersing it in a coolant bath of −78° C. Then, 2.04 g (19.99 mmol, 2.00 eq) of sulfuryl fluoride ($SO_2F_2$) was blown thereinto by using a bomb, followed by stirring at room temperature throughout the night. The reaction-terminated liquid was confirmed by $^1$H-NMR and $^{19}$F-NMR to have a conversion rate and a selectivity of 100% and not less than 70%, respectively. The reaction-terminated liquid was directly distilled (at normal pressure) thereby obtaining halogenated α-fluoroethers represented by the following formula

[Chemical Formula 14]

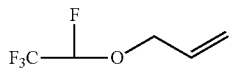

as a mixture of triethylamine and acetonitrile. The yield was confirmed by the conversion rate and the selectivity of the reaction-terminated liquid to be not less than 70%. $^1$H-NMR and $^{19}$F-NMR will be discussed below.

$^1$H-NMR [Standard substance; $(CH_3)_4Si$, Deuteration solvent; $CDCl_3$]; δ ppm/4.30 (dd, 13.2 Hz, 6.0 Hz, 1H), 4.47 (dd, 13.2 Hz, 4.2 Hz, 1H), 5.36 (dd, 16.8 Hz, 0.4 Hz, 1H), 5.40 (dd, 16.8 Hz, 1.2 Hz, 1H), 5.42 (dq, 60.7 Hz, 3.2 Hz, 1H), 5.92 (m, 1H).

$^{19}$F-NMR [Standard substance; $C_6F_6$, Deuteration solvent; $CDCl_3$]; δ ppm/17.95 (dq, 60.7 Hz, 6.0 Hz, 1F), 78.29 (dd, 6.0 Hz, 3.2 Hz, 3F).

Example 3

An excessively small amount of methanol was added to ethyl 3,3,3-trifluoropyruvate and then stirred at room temperature throughout the night, thereby obtaining halogenated hemiacetals represented by the following formula

[Chemical Formula 15]

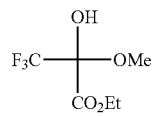

at a quantitative yield.

A pressure-proof reaction vessel made of stainless steel (SUS) was charged with 500 mg (2.47 mmol, 1.00 eq) of halogenated hemiacetals represented by the above formula, 2.5 mL of acetonitrile, 1.000 mg (9.88 mmol, 4.00 eq) of triethylamine and 399 mg (2.47 mmol, 1.00 eq) of triethylamine tris(hydrogen fluoride) complex, followed by immersing it in a coolant bath of −78° C. Then, 505 mg (4.95 mmol, 2.00 eq) of sulfuryl fluoride ($SO_2F_2$) was blown thereinto by using a bomb, followed by stirring at room temperature throughout the night. The reaction-terminated liquid was confirmed by $^1$H-NMR and $^{19}$F-NMR to have a conversion rate and a selectivity of 100% and not less than 70%, respectively.

The reaction-terminated liquid was directly distilled (at from normal pressure to 23 kPa) thereby obtaining halogenated α-fluoroethers represented by the following formula

[Chemical Formula 16]

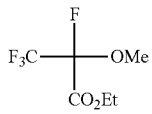

as a mixture of triethylamine and acetonitrile. The yield was confirmed by the conversion rate and the selectivity of the reaction-terminated liquid to be not less than 70%. $^{1}$H-NMR and $^{19}$F-NMR will be discussed below.

$^{1}$H-NMR [Standard substance; $(CH_3)_4Si$, Deuteration solvent; $CDCl_3$]; δ ppm/1.38 (t, 7.2 Hz, 3H), 3.59 (s, 3H), 4.41 (q, 7.2 Hz, 2H).

$^{19}$F-NMR [Standard substance; $C_6F_6$, Deuteration solvent; $CDCl_3$]; δ ppm/26.70 (s, 1F), 80.51 (s, 3F).

The invention claimed is:

1. A process for producing halogenated α-fluoroethers represented by the general formula [2]

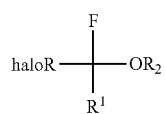

by reacting a halogenated hemiacetal represented by a general formula [1]

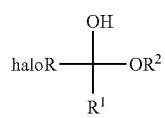

with sulfuryl fluoride ($SO_2F_2$) in the presence of an organic base, wherein: haloR represents haloalkyl group; $R^1$ represents one of hydrogen atom, alkyl group, substituted alkyl group, alkoxycarbonyl group and substituted alkoxycarbonyl group; and $R^2$ represents one of alkyl group and substituted alkyl group.

2. A process for producing a halogenated α-fluoroether bis-derivative represented by a general formula [2a]

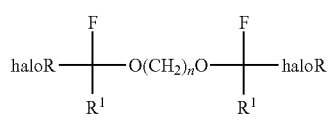

by reacting a halogenated hemiacetal bis-derivative represented by a general formula [1a]

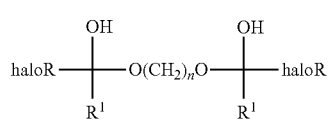

with sulfuryl fluoride ($SO_2F_2$) in the presence of an organic base, wherein: haloR mutually independently represents a haloalkyl group; $R^1$ mutually independently represents one of a hydrogen atom, an alkyl group, a substituted alkyl group, an alkoxycarbonyl group and a substituted alkoxycarbonyl group; and n represents an integer of from 2 to 18.

3. A process for producing one of a halogenated α-fluoroether and a halogenated α-fluoroether bis-derivative, as claimed in claim 1, wherein a reaction of claim 1 is conducted in the additional presence of a salt or a complex of an organic base with hydrogen fluoride in a system.

4. A process for producing a halogenated α-fluoroether represented by a general formula [4]

by reacting a halogenated hemiacetal represented by a general formula [3]

with sulfuryl fluoride ($SO_2F_2$) in the presence of an organic base, wherein $R^2$ represents one of an alkyl group and a substituted alkyl group.

5. A process for producing a halogenated α-fluoroether as claimed in claim 4, wherein a reaction of claim 4 is conducted in the presence of a salt or a complex of an organic base with hydrogen fluoride in a system.

6. A process for producing a halogenated α-fluoroether represented by a general formula [6]

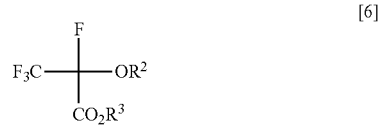

by reacting a halogenated hemiacetal represented by a general formula [5]

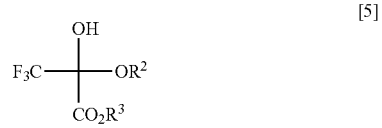

with sulfuryl fluoride ($SO_2F_2$) in the presence of an organic base, wherein $R^2$ and $R^3$ mutually independently represent one of an alkyl group and a substituted alkyl group.

7. A process for producing a halogenated α-fluoroether as claimed in claim 6, wherein a reaction of claim 6 is conducted in the additional presence of a salt or a complex of an organic base with hydrogen fluoride in a system.

* * * * *